US010029073B2

(12) United States Patent
Kabe et al.

(10) Patent No.: US 10,029,073 B2
(45) Date of Patent: Jul. 24, 2018

(54) STEERABLE ASSEMBLY FOR SURGICAL CATHETER

(71) Applicant: ABBOTT CARDIOVASCULAR SYSTEMS INC., Santa Clara, CA (US)

(72) Inventors: Arundhati N. Kabe, Sunnyvale, CA (US); Troy L. Thornton, San Francisco, CA (US); Aaron M. Weiss, San Francisco, CA (US)

(73) Assignee: ABBOTT CARDIOVASCULAR SYSTEMS, INC., Santa Clara, CA (US)

( * ) Notice: Subject to any disclaimer, the term of this patent is extended or adjusted under 35 U.S.C. 154(b) by 836 days.

(21) Appl. No.: 13/675,934

(22) Filed: Nov. 13, 2012

(65) Prior Publication Data
US 2014/0135685 A1 May 15, 2014

(51) Int. Cl.
*A61M 31/00* (2006.01)
*A61M 25/01* (2006.01)
*A61B 1/008* (2006.01)
*A61B 17/00* (2006.01)

(52) U.S. Cl.
CPC .... *A61M 25/0141* (2013.01); *A61M 25/0138* (2013.01); *A61M 25/0147* (2013.01); *A61B 1/008* (2013.01); *A61B 2017/00314* (2013.01); *A61B 2017/00323* (2013.01); *A61B 2017/00783* (2013.01); *A61M 2025/0161* (2013.01)

(58) Field of Classification Search
CPC .............. A61M 25/01; A61M 25/1047; A61M 25/0141; A61M 25/0138; A61M 25/0133; A61M 2025/015; A61M 2025/0161; A61M 25/0147; A61M 2025/0138; A61M 2025/0687; A61B 2017/00318; A61B 2017/00323; A61B 1/008; A61B 2017/00783; A61B 2017/00314
USPC ............................ 604/95.01, 95.04; 600/141
See application file for complete search history.

(56) References Cited

U.S. PATENT DOCUMENTS

| 5,042,707 | A | 8/1991 | Taheri et al. |
| 7,338,505 | B2 * | 3/2008 | Belson ............... A61B 1/00147 600/146 |
| 7,637,903 | B2 | 12/2009 | Lentz et al. |
| 7,708,102 | B2 | 5/2010 | Takehara et al. |
| 8,096,457 | B1 | 1/2012 | Manoux et al. |
| 2002/0082585 | A1 | 6/2002 | Carroll |
| 2003/0083550 | A1 * | 5/2003 | Miyagi ........................ 600/141 |

(Continued)

OTHER PUBLICATIONS

International Search Report dated Jul. 18, 2013.

*Primary Examiner* — Kami A Bosworth
*Assistant Examiner* — Tiffany Legette-Thompson
(74) *Attorney, Agent, or Firm* — David J. Pitman; Fulwider Patton LLP

(57) ABSTRACT

A catheter configured for intraluminal delivery to a location in the body of a patient, the catheter comprising a steerable assembly comprising a first segment connected to a second segment; the first segment comprises first and second cylindrical elements connected to each other by a first revolute joint in a first single plane; the second segment comprises third and fourth cylindrical elements connected to each other by a second revolute joint in a second single plane, wherein the first single plane and the second single plane are offset by an angle from each other.

28 Claims, 7 Drawing Sheets

(56) References Cited

U.S. PATENT DOCUMENTS

| | | | |
|---|---|---|---|
| 2005/0107667 A1* | 5/2005 | Danitz | A61B 1/0053 600/139 |
| 2006/0111616 A1* | 5/2006 | Danitz | A61B 1/0055 600/142 |
| 2008/0287741 A1 | 11/2008 | Ostrovsky | |
| 2011/0022078 A1 | 1/2011 | Hinman | |
| 2012/0190924 A1 | 7/2012 | Tseng | |

* cited by examiner

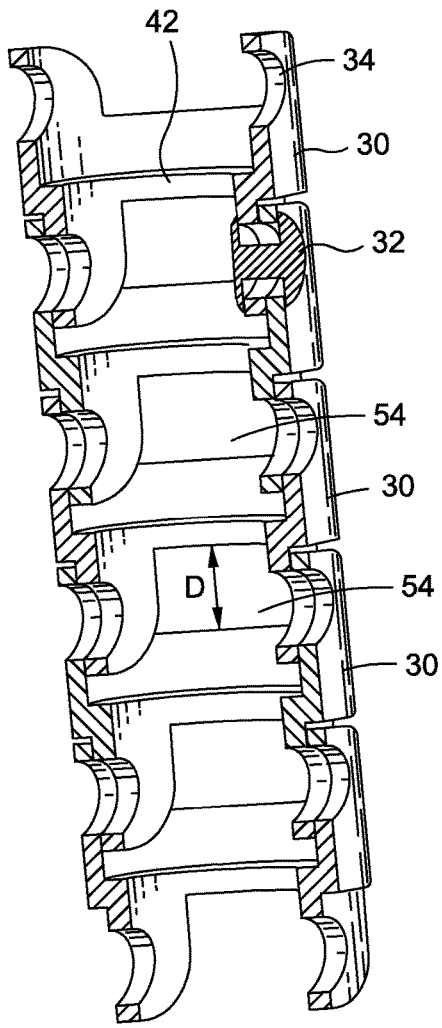
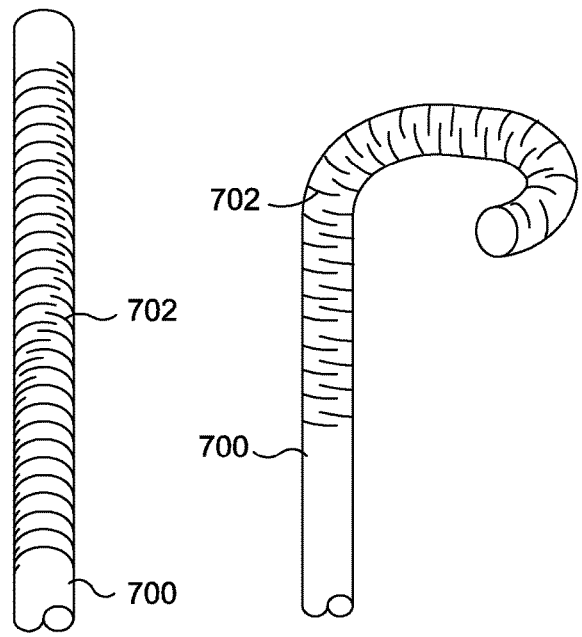
FIG. 18
(PRIOR ART)
FIG. 19
(PRIOR ART)
FIG. 17
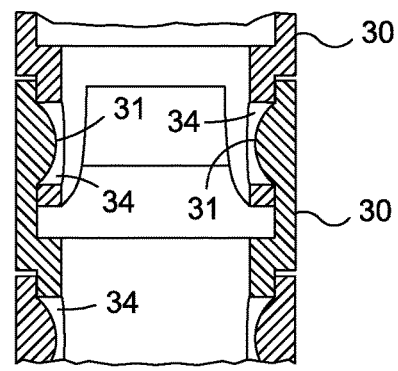
FIG. 20

STEERABLE ASSEMBLY FOR SURGICAL CATHETER

BACKGROUND

This invention relates to catheters that can by steered by external controls. More particularly the invention relates to such catheters that can assume three dimensional curves.

Modern medical procedures rely ever more upon minimally invasive access to organs and tissues of a patient, frequently via body lumens such as veins or arteries. A common feature of most such procedures is that a medical device may be carried at the distal tip of a catheter, or may be inserted to the tip of a steerable assembly, to a desired location in the body of a patient, where it may be activated. For example, one or more electrodes may be provided at the distal end of a catheter for purposes of tissue ablation; inflatable balloons may be provided for purposes of vessel expansion, or for separating tissue layers to create a space to perform a further procedure; blades or rotating burrs may be provided for purposes of clearing a blocked lumen; or, needles may be provided for injecting agents into body tissue. Various steering mechanisms for catheters carrying such devices have heretofore been developed and used.

Physicians have used a number of different catheters and techniques, each of which provides a different characteristic. Some catheters have been developed that allow a physician to move a distal end of a catheter in any direction, thereby permitting the physician to steer a tool to the desired location. In some circumstances, this is a useful advantage, in that it allows a physician freedom to move a catheter tip in a direction that could not be anticipated beforehand.

However, problems persist in the art of steerable catheters in applications such as the foregoing. In certain applications, a physician may be confronted with an extremely tortuous luminal passageway in the body of a patient to navigate, but where the general shape of the tortuous passageway can be predicted beforehand. An example is in the case of cardiac surgery, such as mitral valve repair. During mitral valve repair, the process will typically comprise accessing a patient's vasculature at a location remote from the heart such as the iliac artery in the thigh, advancing an interventional tool through the vasculature to a ventricle and/or atrium in the heart, and engaging the tool for its designed purpose. By engaging the tool, the tissue structure of the valve may be modified in a manner that reduces valve leakage or regurgitation during ventricular systole. Typically, once the interventional tool has been advanced all the way from the remote access point to the heart using a steering feature that has been provided, the physician must position the tool in the heart in such a manner that allows the physician to manipulate the catheter in relation to the target tissue. At this point, a problem may arise in that the steerable portion of the catheter at the distal end does not permit the physician enough control over the tool attached to the distal end of the catheter. This phenomenon may arise because the steerable portion may have the capability of changing its position under the application of slight external forces such as may naturally occur within the patient's anatomy. Thus, just when a physician believes the tip of the catheter is in the correct place to conduct the intended procedure, the tip of the catheter may change its position without the physician applying any additional force via pullwires such as may be used to steer the catheter, and this effect may thereby disrupt the procedure until the tip is repositioned. The problem may persist even when, with reference to FIGS. 18 and 19, a steerable assembly is formed, according to methods known in the art, from a long tube 700 with slits 702 formed in the wall of the tube with the intention of ultimately providing a pre-shaped configuration to the tube, as exemplified in FIG. 19. The problem here arises when opposing pullwires, for pulling the distal tip of the tube from one side to the other, are freely extended up the bore of the tube and are connected to opposing sides at the distal tip of the tube. Yet a further problem may tend to arise with the kind of steerable assembly disclosed in FIGS. 18 and 19, for, although the slits in the tube wall may enable the tube to bend, the radius of curvature of the bend may not be sufficiently small to satisfy the desired shape of the assembly.

Thus there is a need in the art for a catheter that addresses the shortcomings of the prior art. The present inventive concept aims at reducing at least some of the shortcomings of the prior art.

SUMMARY OF THE INVENTION

According to a first aspect of the inventive concept, there is provided a catheter configured for intraluminal delivery to a location in the body of a patient. The catheter comprises an elongate hollow tubular body having a proximal end and a distal end. A steerable assembly is attached to the distal end of the tubular body. The steerable assembly comprises a first segment connected to a second segment. The first segment comprises first and second elements, each element defining an internal bore and connected to each other by a first revolute joint configured to bend in a first single plane, the first revolute joint being a bearing joint. The scope of this type of joint will be described more fully below. The second segment comprises third and fourth elements each element defining an internal bore and connected to each other by a second revolute joint configured to bend in a second single plane, the second revolute joint being a bearing joint. The first single plane and the second single plane are offset by an angle from each other. For example, the offset angle may be 30, 45, 90, 120, 135 degrees or the like. However, in a preferred embodiment, the angle is 90 degrees. In one aspect, the first segment and the second segment are connected to each other by an intermediate cylindrical element.

In one embodiment, the first segment further comprises a fifth element defining an internal bore, and connected to the second element by a third revolute joint configured to bend in the first single plane, the third revolute joint being a bearing joint. A sixth element defining an internal bore may be provided, and connected to the fourth element by a fourth revolute joint configured to bend in the second single plane, the fourth revolute joint being a bearing joint.

In some embodiments, the first segment and the second segment are connected to each other by an intermediate element.

In some embodiments, the first revolute joint may be formed to include a first opening in the first element and a second opening in the second element, and a pin provided to pass through the first and second openings. In other embodiments, the first revolute joint may be formed to include a depression in the first element and a protrusion on the second element, wherein the protrusion is configured to fit within the depression to permit rotation of the elements with respect to each other.

In some embodiments, the first revolute joint may be formed to include a ball portion on the first element and a socket portion on the second element, wherein the socket portion is configured to receive the ball portion and to permit the ball portion to rotate while in contact with the socket portion. In further embodiments, the steerable assembly may further include a flexible membrane configured to permit the elements of the assembly to rotate in relation to each other, but to restrain the elements from axial movement in relation to each other. Preferably, the membrane may be applied at an outside diameter surface of the steerable assembly.

In yet further embodiments, the catheter may further include a plurality of pullwires extending through the tubular body and through the steerable assembly, wherein each of the first, second, third and fourth elements defines at least one detent configured to receive one of the pullwires. In some embodiments, the at least one detent is a hole defining a complete continuous circumference. In yet further embodiments, the steerable assembly defines an internal bore, the bore being sized and configured to receive one of a catheter, an interventional device, or an operating cable for operating a surgical device attached to the catheter distal of the steerable assembly.

The inventive concept thus described provides an advantageous solution which prevents the distal end of the catheter from being so flexible or "floppy" that it denies the surgeon the required degree of control. The inventive concept limits the extreme distal end of the catheter to having only one degree of bending freedom, and does not allow the distal end to bend in simply any direction—as may apply when it has two degrees of bending freedom. Under two degrees of bending freedom, the distal end would disadvantageously have the capability of changing position under the application of only slight external forces such as may naturally occur within the patient's anatomy through respiration and the like.

Furthermore, by arranging the wires in detents in accordance with the principles of the inventive concept, this tends to prevent the outcome that both wires may be relocated to only one side of the tube in the vicinity of a bend—an effect that may cause the wires to lose their ability to apply opposing forces over the whole length of the tube for bending the tube left or right as desired, and may instead cause the tube to bend in only one direction (i.e. only left, or only right), The described configuration of the steerable assembly allows for a structure that is both steerable, and that can adopt a stable preformed shape once it is positioned within the targeted body organ of a patient. Unlike a steerable assembly that is capable of two degrees of bending freedom at every point along its length, and which can therefore potentially buckle uncontrollably in any direction, the steerable assembly of the present embodiment is capable of only one degree of bending freedom at any point along its length. Thus, when the pullwires are fully activated by tensioning, the steerable assembly is capable of being effectively locked into a pre-designed desired shape that cannot be altered by accidental forces on the exterior of the assembly, such as may occur within the anatomy of a patient during such procedures. There is no tendency toward instability such as by buckling that would allow the shape of the steerable assembly to change accidentally.

According to a second aspect of the inventive concept, there is provided a catheter configured for intraluminal delivery to a location in the body of a patient. The catheter comprises an elongate hollow tubular body having a proximal end and a distal end. A steerable assembly is attached to the distal end of the tubular body and comprises a first, a second, and a third element, each element defining a central bore. The first and second elements are connected to each other by a first revolute joint configured to bend in a first single plane, the first revolute joint being a bearing joint. The second and third elements are connected to each other by a second revolute joint configured to bend in a second single plane, the second revolute joint being a bearing joint. The first single plane and the second single plane are offset from each other by an angle, preferably the offset angle is 90 degrees. In some embodiments, the first revolute joint is formed to include a first opening on the first element and a second opening on the second element, and a pin is configured to pass through the first and second openings. In another embodiment, the first revolute joint is formed to include a depression in the first element and a protrusion on the second element, wherein the protrusion is configured to fit within the depression to permit rotation of the elements with respect to each other. In yet other embodiments, the first revolute joint is formed to include a ball portion on the first element and a socket portion on the second element, wherein the socket portion is configured to receive the ball portion and to permit the ball portion to rotate while in contact with the socket portion. In a preferred aspect of the latter embodiment, the steerable assembly further includes a flexible membrane configured to permit the elements of the assembly to rotate in relation to each other, but to restrain the elements from axial movement in relation to each other. Preferably, the membrane is applied to an outside diameter surface of the steerable assembly.

In some embodiments, a plurality of pullwires are provided to extend through the tubular body and through the steerable assembly. Preferably, each of the first, second, and third elements defines at least one detent configured to receive one of the pullwires. In other embodiments, the steerable assembly defines an internal bore, the bore being sized and configured to receive an operating cable for operating a surgical device attached to the catheter distal of the steerable assembly.

According to a third aspect of the inventive concept, there is provided a catheter configured for intraluminal delivery to a location in the body of a patient. The catheter comprises an elongate hollow tubular body having a proximal end and a distal end. A steerable assembly is attached to the distal end of the tubular body. A plurality of pullwires extends through the tubular body and through the steerable assembly. The steerable assembly comprises a first segment connected to a second segment. The first segment comprises first and second elements connected to each other by a first revolute joint configured to bend in a first single plane. The second segment comprises third and fourth elements connected to each other by a second revolute joint configured to bend in a second single plane, wherein the first single plane and the second single plane are rotationally offset by an angle from each other, preferably the angle is 90 degrees. Preferably, each of the first, second, third and fourth elements defines means for holding the pullwires at a predetermined location in relation to the elements. Each element is provided with a space that will allow one element to freely rotate to a limited degree in relation to an adjacent element. In some embodiments, the first element and the second element are connected in the first revolute joint to each other by at least one pin passing through a first hole in the first element and a second hole in the second element, whereby the first element and the second element rotate about the pin. In other embodiments, the first element defines a ball portion and the second element defines a socket portions, wherein the socket portion is configured to receive the ball portion and to permit the ball portion to rotate while in contact with the socket portion. In other embodiments, the first segment and the second segment are each connected to an intermediate element, wherein the intermediate element and the first segment are connected by a third revolute joint in the first single plane, and the intermediate element and the second segment are connected by a fourth revolute joint in the second single plane. In some embodiments, the steerable assembly further includes a flexible membrane configured to permit the elements to rotate in relation to each other, but to substantially restrain the elements from axial movement in relation to each other. Preferably, the membrane is applied to an outside diameter surface of the steerable assembly. In some embodiments, the at least one detent is four detents, and the plurality of pullwires is four pullwires, each detent being spaced apart from an adjacent detent. Preferably, the steerable assembly defines an internal bore, the bore being sized and configured to receive an operating cable for operating a surgical device attached to the catheter distal of the steerable assembly.

These and other advantages of the inventive concept will be appreciated when read in conjunction with the figures and the detailed description of the preferred embodiments.

BRIEF DESCRIPTION OF THE DRAWINGS

FIG. 4 is a schematic view showing an exemplary application of the distal portion of the catheter in FIG. 3a.

FIG. 17 is a sectional view (shown with a slight perspective) of the embodiment in FIG. 5.

FIG. 18 is a perspective view of structure known in the prior art, shown in a first straight condition.

FIG. 19 is a view of the structure in FIG. 18, shown in a bent condition.

FIG. 20 is a sectional view of a variation of the previous embodiments.

DETAILED DESCRIPTION OF THE PREFERRED EMBODIMENTS

With reference to the figures, preferred embodiments of the invention are described. The specification discloses features of a bendable and steerable assembly that can be bent in compound and complex ways for greater maneuverability within the body and, ultimately, enhanced efficacy of the operative device carried by the bendable assembly, which, in some embodiments, may be a catheter, or may be configured to receive a catheter through a central bore. The illustrated and preferred embodiments disclose and describe these structures, systems, and techniques in relation to mitral valve repair, although the same may be used in conjunction with any procedure requiring complex maneuverability.

Figure 1:
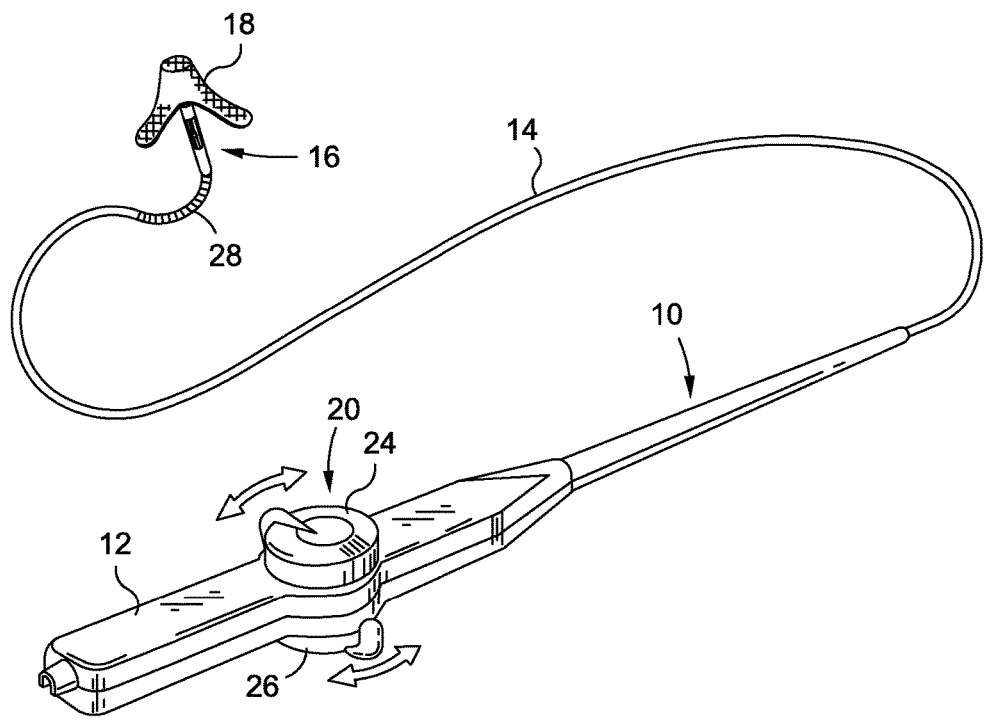
FIG. 1 is a schematic perspective view of a catheter having features of the present invention.

FIG. 1 shows a catheter 10, which includes features of the invention. The catheter 10 includes a handle 12 and a flexible tubular catheter body 14. In the illustrated and exemplified embodiment of the catheter, the distal region 16 may, for example, carry a clip device 18 for performing mitral valve repair, or other surgical or therapeutic device 18' mounted on an independent catheter 38' and independently slidable within the tubular body 14.

The catheter 10 shown in FIG. 1 includes on the handle 12 a steering mechanism 20. The mechanism 20 includes two control knobs 24 and 26 on the handle 12, which can be individually manipulated by the physician.

As will be described in greater detail below, the steering mechanism 20 may be coupled to a compound steerable assembly 28, which is carried within the distal region 16 of the catheter body 14. Operation of the control knobs 24 and 26 bend the steerable assembly 28 to flex the distal region 16 (as FIG. 1 generally shows) in ways that aid in orienting the clip device 18 (FIG. 3a) or other device 18' (FIG. 3b) in a desired direction.

Figure 3A:
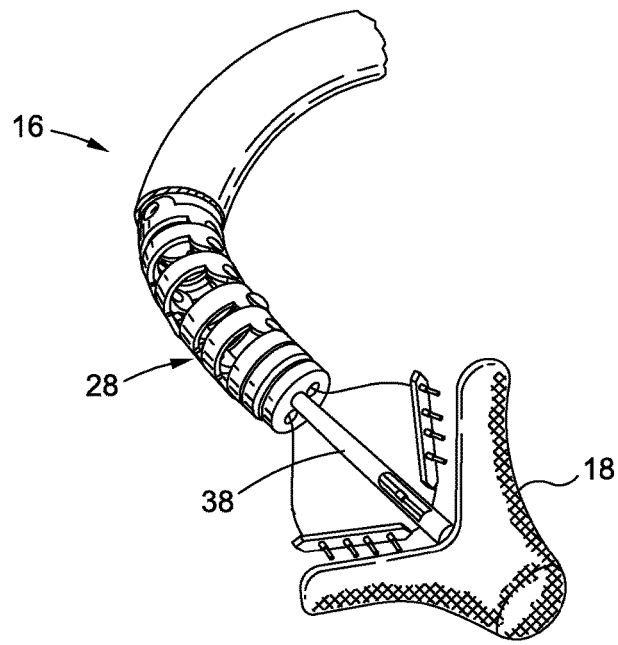
FIG. 3a is a detailed view of a distal portion of the catheter shown in FIG. 1, in which a terminal steerable assembly is shown in conjunction with an interventional device.
Figure 3B:
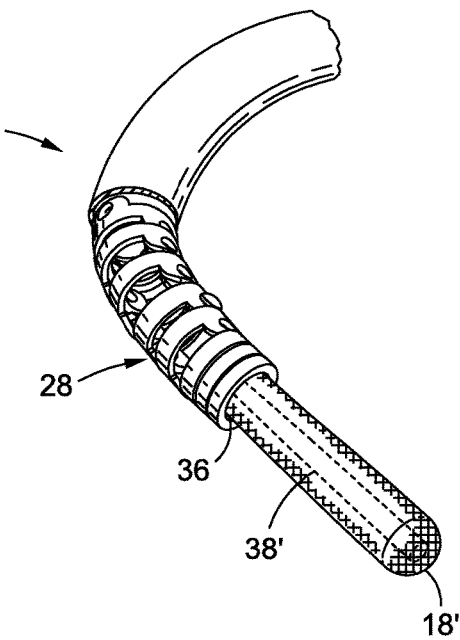
FIG. 3b is a detailed view of a distal portion of the catheter shown in FIG. 1, in which a terminal steerable assembly is shown in conjunction with an independent catheter extending through the steerable assembly.
Figure 4:
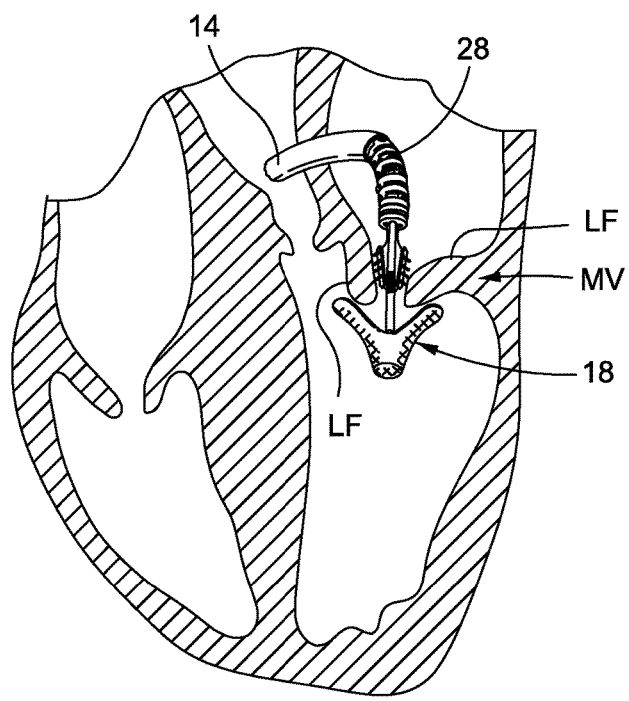

FIG. 3a shows one embodiment of a compound steerable assembly 28 in conjunction with the distal portion 16 of a catheter. FIG. 4 shows how the compound steerable assembly 28, mounted at the distal end 16 of the catheter, may be used in the exemplified embodiment, for repairing the mitral valve of a patient's heart. FIG. 3b shows another embodiment, in which a compound steerable assembly 28 is used for creating a passageway of desired bent configuration for delivering an catheter 38' independently slidable within the catheter body 14 to a desired location through a central bore of the assembly.

Figures 5, 6:
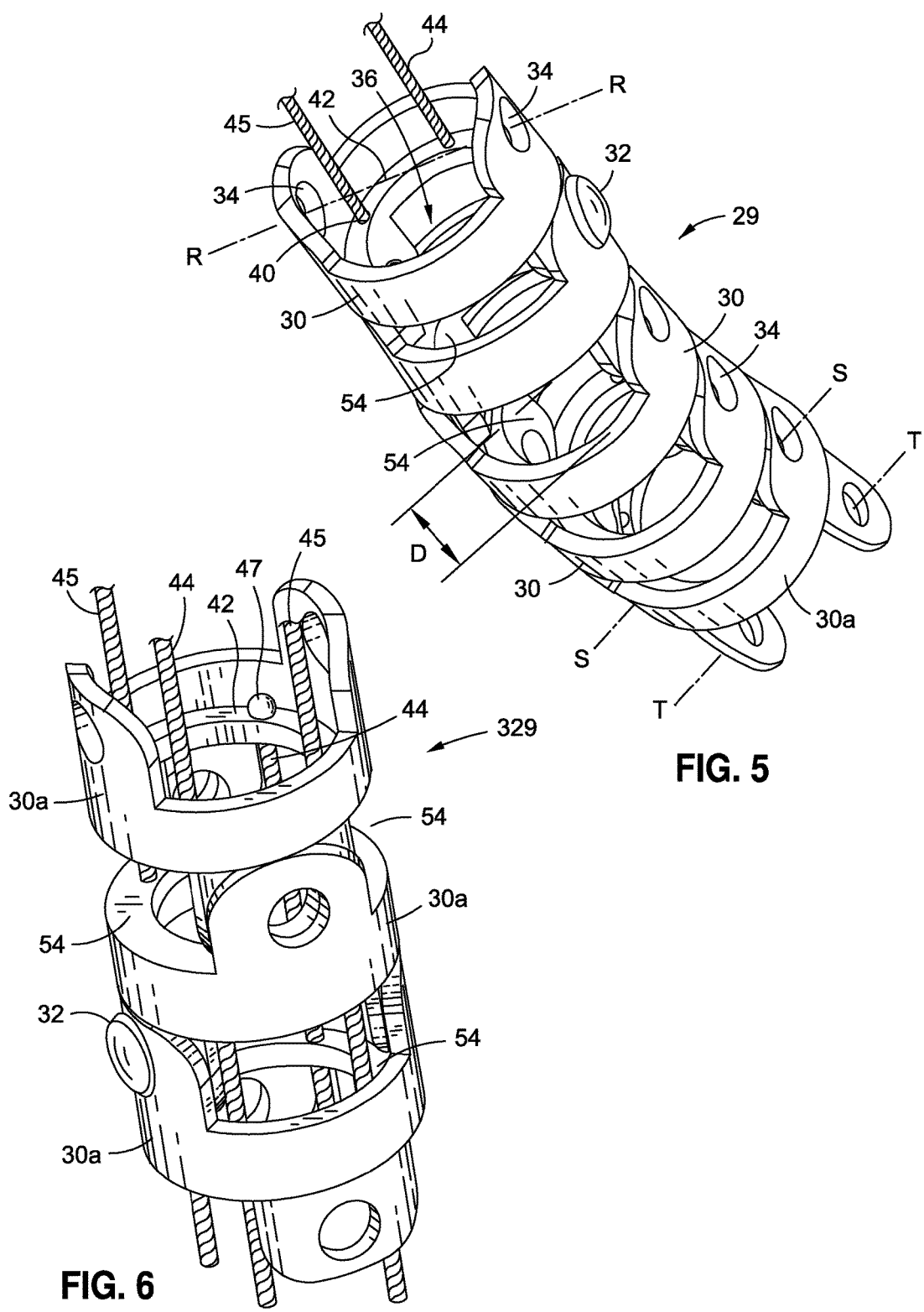
FIG. 5 is a perspective view of an embodiment of a segment having features of the invention.
FIG. 6 is a perspective view of another embodiment of a segment having features of the invention.
Figure 7:
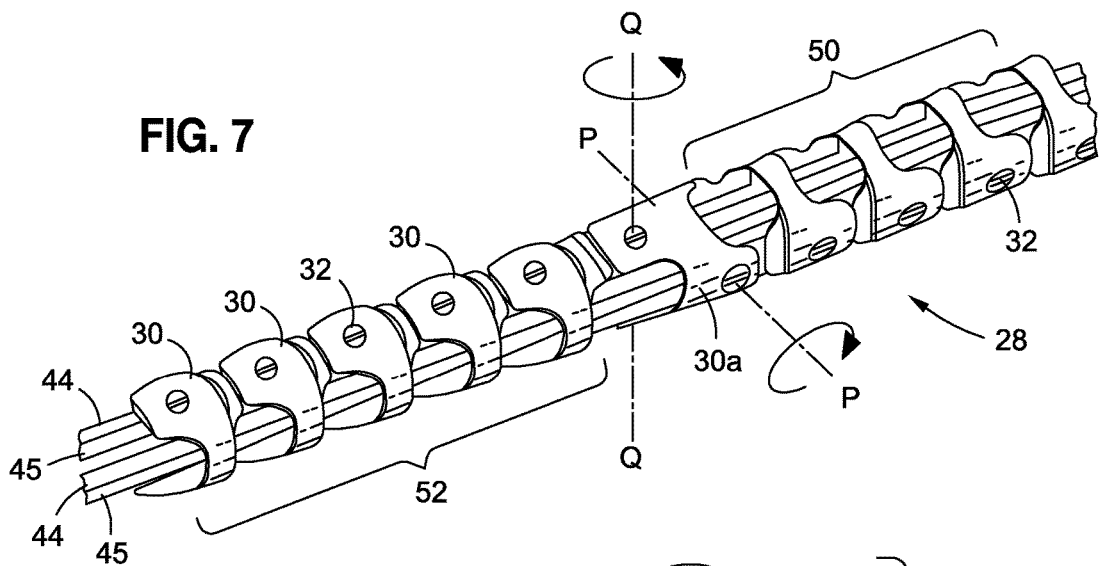
FIG. 7 is a perspective view of a steerable assembly having features of the invention, shown in a first straight condition.
Figure 8:
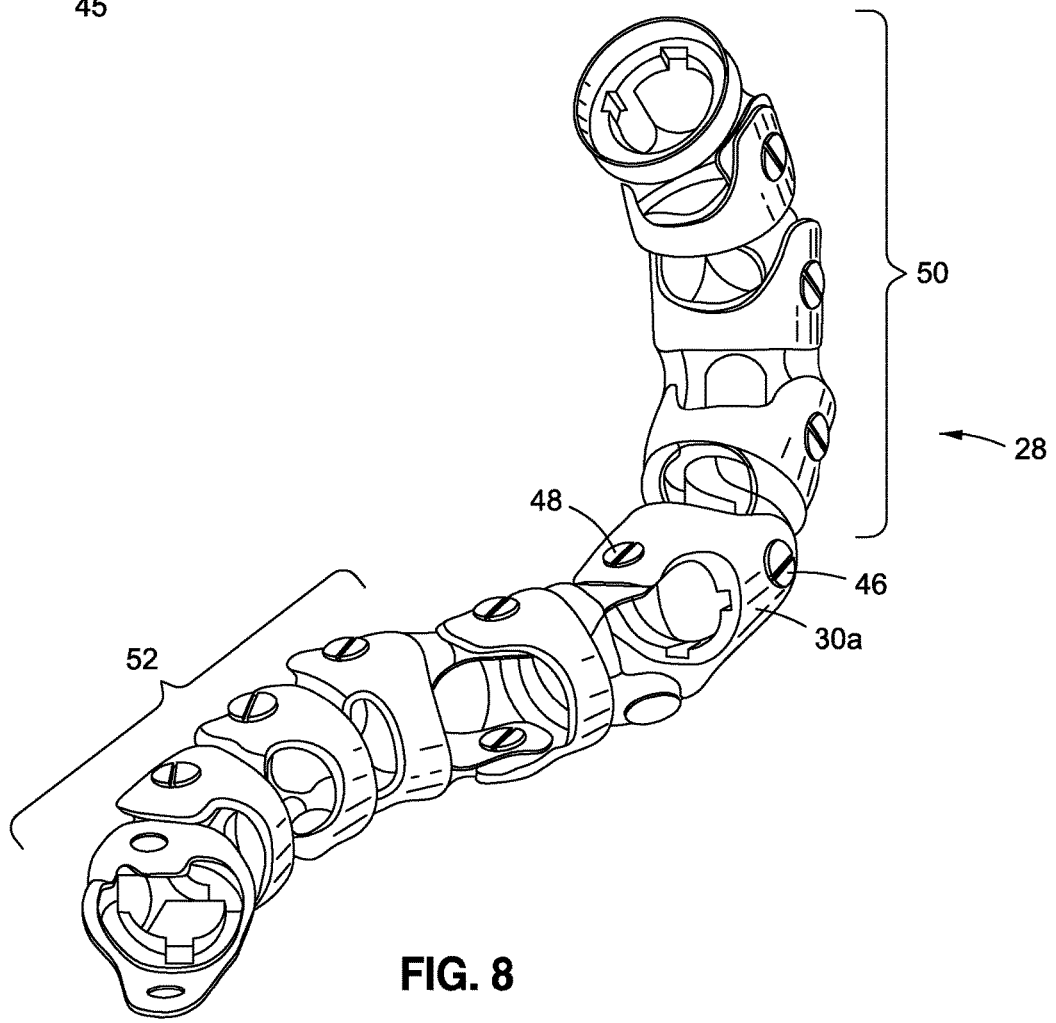
FIG. 8. is a perspective view of the steerable assembly of FIG. 7, shown in a second curved condition.
Figure 9:
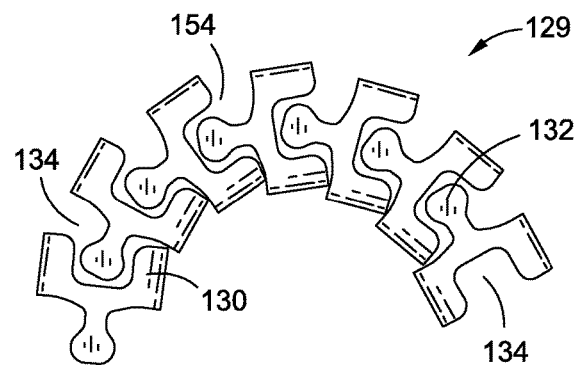
FIG. 9 is a side elevational view of a further embodiment of a segment having features of the invention shown in a curved condition.
Figure 10:
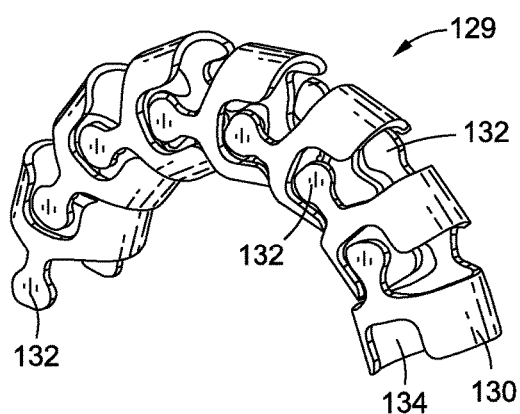
FIG. 10 is an oblique perspective view of the segment shown in FIG. 9.
Figure 11:
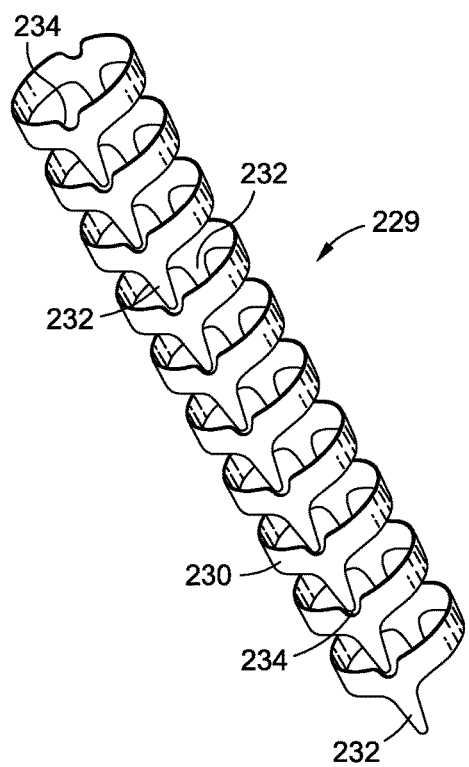
FIG. 11 is a perspective view of yet another embodiment of a segment having features of the invention, shown in a first condition.
Figure 12:
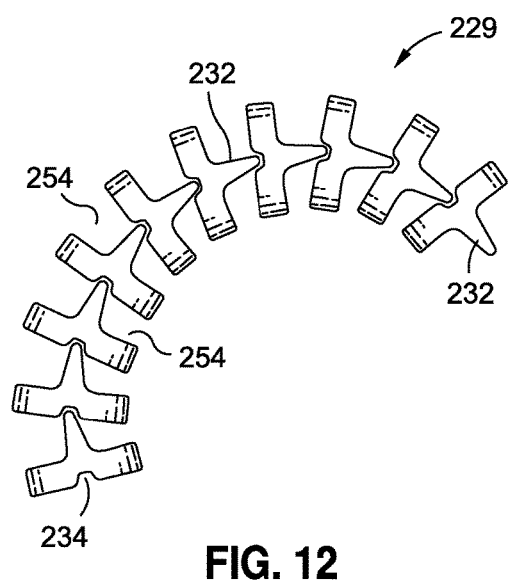
FIG. 12 is a perspective view of the embodiment of FIG. 11, shown in a second condition.

FIG. 5 exemplifies a segment 29 which is a component of an exemplary first embodiment of the compound steerable assembly 28 (seen as a whole in FIGS. 7 and 8). The segment 29 of the present embodiment is comprised of a plurality of initially separate (i.e., discrete) cylindrical elements. In the present embodiment, the cylindrical elements are identified by the numeral 30. Each cylindrical element 30 is combined into the segment 29 to be in contact with an adjacent cylindrical element to form a segment having an elongate tubular form. Each cylindrical element 30 is configured to be connected to, and to move in relation to, an adjacent cylindrical element by a revolute joint in a single plane. The term "revolute joint in a single plane" is used herein to mean that two cylindrical elements in contact with each other rotate in relation to each other, and throughout rotation only one degree of bending freedom is achievable.

Another aspect of the joint between the cylindrical elements 30 is that it is a bearing joint, by which it is meant that opposing surfaces of each cylindrical element slide past each other, or roll against each other, during rotation of the joint. One advantage provided by a bearing joint as described is that it will tend to provide a smaller radius of curvature to a bend between two elements than can be provided by a joint that renders two elements continuously connected to each other by a continuum of material. A bearing joint of the kind described may be achieved, as in the present embodiment exemplified in FIG. 5, by snaps or pins, arranged to rotatably join two adjacent cylindrical elements 30 at two points of contact and aligned on a diametric axis, such as axis R-R. In the present embodiment, this may be achieved by passing a pin 32 through each of two openings 34 present in each cylindrical element 30. (For clarity, only one pin 32 is shown in FIG. 5, and also in FIG. 6. However, while in operation, a pin 32 will be inserted in each opening 34.) Thus, in the case of the embodiment in FIG. 5, the cylindrical elements 30 slide past each other in the vicinity of the openings 34 (while bearing against a common pin 32) during rotation of the joint. Alternatively (as exemplified in FIG. 20), one element 30 may be provided with two males snaps 31 that are configured to snap fit into female depressions such as exemplified in FIG. 20. In FIG. 20, the female depressions are shown as being the same as openings 32, but depressions having other shapes are contemplated to be within the scope of the invention. It will be appreciated that these joints also are bearing joints. It may be noted that snaps have an advantage over pins in that they facilitate the assembly of a segment made up from multiple cylindrical elements. As contemplated herein, a snap residing in a depression will tend to keep the elements from separating axially, while allowing rotation of one snap in relation to another.

In yet other embodiments, described below, different means for achieving such a revolute joint, which is also a bearing joint, may be used.

As may be seen in FIG. 5, a plurality of cylindrical elements 30 may be connected to one another in series as described above, to provide an elongate segment 29 suitable for use in a steerable assembly. The cylindrical elements 30 are configured to provide the segment 29 with a central bore 36 that has an open diameter large enough to permit access by an interventional device 38 (as seen in FIG. 3a) that will operate the clip device 18 at the tip of the catheter. In some applications, the steerable assembly 28 and the central bore 36 may be configured to admit a catheter 38' (as seen in FIG. 3b) that is configured to be independently inserted through the bore after the segment has been placed in the anatomy to the satisfaction of the surgeon. Such a catheter 38' may carry for example a thermal ablation device 18', or other such surgical or therapeutic device, as desired.

In one aspect, the points of contact between one cylindrical element 30 and the next may be positioned so that all the successive revolute joints of the segment so formed cause each successive cylindrical elements to bend, in relation to the previous cylindrical element, in the same single plane. As a result, the entire segment 29 may be configured to assume a continuously bent form that lies in a single plane. The resulting segment 29 is suitable for use as a component of a steerable assembly 28 (seen in FIGS. 7 and 8) having features of the present invention. It will be appreciated that, because a cylindrical element 30 may be connected to an adjacent element both in front and behind, a typical cylindrical element 30 will have two sets of two holes or snaps per set, the holes or snaps of the first set 34 lying on an axis S-S, and of the second set 35 on an axis T-T.

It will be appreciated that to accomplish the described bending of each joint in the segment 29 in the same plane, the axes S-S and T-T in each element 30 must be parallel, as exemplified in FIG. 5. To align a set of holes or snaps of one element 30 with the holes or snaps of an adjacent element, it may be necessary to configure each element so that a forward set of holes or snaps (on axis S-S) occupies a larger spacing across the diameter of the cylindrical element, and a rearward set of holes or snaps (on axis T-T) occupies a smaller spacing across the diameter of the element, as may be appreciated with respect to FIG. 5. This allows limitless extension of the segment by adding similar elements 30.

In another aspect (for which a figure is not provided), the points of contact between one cylindrical element 30 and the next may be positioned so that all the successive revolute joints of the segment so formed cause each successive cylindrical elements to bend, in relation to the previous cylindrical element, in a plane that is offset from the previous plane by a slight rotation. It will be appreciated that this configuration may impart a slight helical spiral, as may be desired, to the segment when it is in a bent condition.

In order for a physician to steer and direct the segment 29 in a steerable assembly, a plurality (preferably two) of pullwire sets 44, 45 may preferably be added to the segment, as exemplified in FIG. 5 (where only one wire of each set is shown to maintain clarity, but FIG. 6 shows two wires in each set). Under this configuration, each cylindrical element 30 is configured to support four pull wires to pass adjacent the surface of an internal diameter surface of the bore 36, thereby keeping the pullwires away from the middle of the bore of the segment, where the interventional device 38 or catheter 38' (seen in FIGS. 3a and 3b) will be positioned and therefore where open space is needed for the assembly 28 to successfully operate. To achieve this result, detents 40 may be formed in an internal flange 42 of each cylindrical element 30. In some embodiments the detent 40 may be a hole with a continuous circumference as exemplified in FIG. 5, but the detents may also be incomplete circumferential openings configured to permit a pullwire to be snapped in from the side rather than requiring the pullwire to be fed through from one end to an opposite end of a hole. It will be appreciated that snapping a pullwire into a detent from the side will facilitate assembly of a segment because it avoids the more laborious process of threading the pullwire through each and every hole. During manufacture and assembly of the steerable assembly, the cylindrical elements 30 are preferably connected to each other in serial fashion. Before applying the pins 32 or snaps that will hold two sequential cylindrical elements together, the pullwire sets 44, 45 may be passed through the detents 40. Thus, the pullwires are given support over the length of the segment 29, and are constrained to reside adjacent an inside tubular wall surface of the bore 36. As a result, when one set of the diametrically opposing sets of pullwires is tensioned, it will tend to compress the side of the segment closest to the tensioned wires. To permit bending of the segment, each cylindrical element is provided with a space 54 that will allow one cylindrical element to freely rotate to a limited degree in relation to an adjacent cylindrical element. However, the space 54 is given only a limited axial depth "D" (indicated in FIG. 5) so that the angle of rotation is limited to a desired magnitude before one cylindrical element 30 butts up into an adjacent cylindrical element. This limit may contribute to prevent the steerable assembly from being too "floppy"—i.e. having too much latitude for bending. Furthermore, the depth "D" of the space 54 is selected to provide the steerable assembly with a predetermined curved shape so that once the steerable assembly 28 has delivered the distal end 16 to its desired location within the patient's anatomy, the act of fully tensioning the appropriate pullwires in the sets 44, 45 will cause the steerable assembly to assume a desired pre-designed final configuration.

With reference to FIGS. 7 and 8, in one embodiment, the assembly 28 is formed by connecting together at least two segments 50, 52 of the kind described above. A special cylindrical element 30a may be used at the point of connection between the segments that is different from the cylindrical elements 30 described above. Here, the special cylindrical element 30a is configured to impart a rotation between the single plane occupied by the joints of one segment, and the single plane occupied by the joints of the next segment. This effect is exemplified in FIGS. 7 and 8. The special cylindrical element 30a has two sets of holes, with two holes per set. One hole set 46 is for connection to a first segment 50, and another hole set 48 is for connection to a second, adjacent, segment 52 (FIG. 8). The first hole set is aligned in a first axis P-P, and the second hole set is aligned in a second axis Q-Q (FIG. 7). The second axis is rotated preferably by 90 degrees with respect to the first axis. This has the result that, while the first segment 50 can bend in a first single plane extending up and down, the second segment 52 can bend in a second single plane extending left and right, as exemplified in FIG. 8. Connecting the two segments 50, 52 together is the special cylindrical element 30a. In order to produce a specific desired final shape of a steerable assembly 28, it may be necessary to terminate some pullwires at different axial locations along the assembly. A pullwire termination is exemplified in FIG. 6, where one pullwire 44 is shown terminated on a flange 42 by a tie 47 that may be formed from an epoxy, solder, or by crimping the wire into a thickened portion to resist retraction through the hole 40.

The described configuration of the steerable assembly 28 allows for a structure that is both steerable, and that can adopt a stable preformed shape once it is positioned within the targeted body organ of a patient. Unlike a steerable assembly that is capable of two degrees of bending freedom at every point along its length, and which can therefore potentially buckle uncontrollably in any direction, the steerable assembly of the present embodiment is capable of only one degree of bending freedom at any point along its length. Thus, when the pullwire sets are fully activated by tensioning, the steerable assembly is capable of being effectively locked into a pre-designed desired shape that cannot be altered by accidental forces on the exterior of the assembly, such as may occur within the anatomy of a patient during such procedures. There is no tendency toward instability such as by buckling that would allow the shape of the steerable assembly 28 to change accidentally.

Figure 2:
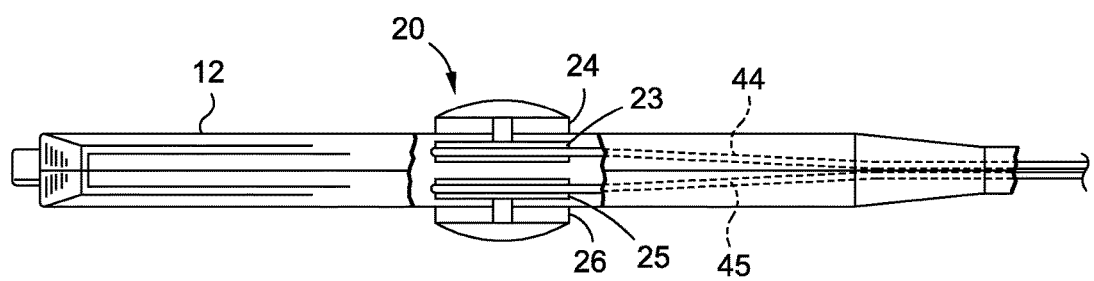
FIG. 2 is a plan view of a handle of the catheter shown in FIG. 1.

As FIG. 2 shows, the control knobs 24 and 26 are individually coupled to rotatable cam wheels, respectively 23 and 25, within the handle 12. Rotation of the respective knob 24 and 26 serves to rotate its respective cam wheel. The two sets of steering wires 44, 45 are attached to the cam wheels, one set to each, and each wire in a set extending through the steerable assembly on diametrically opposite sides of the internal bore. The first set 44 is offset from the second set 45 by 90 degrees.

Rotation of the cam wheel 23 (by manipulation of the knob 24) in a first direction, pulls upon a first one of the first set of steering wires 44. Rotation of the cam wheel 25 (by manipulation of the knob 26) in a first direction, pulls upon a first one of the second set of steering wires 45. Rotation of each cam wheel in an opposite second direction pulls upon the second wire in each set of wires 44, 45. Thus, by rotating the knobs 24, 26 one way or the other, the two sets of wires 44, 45 may apply forces capable of directing the first segment 50 up or down, and the second segment 52 left or right. Additional structure (not shown) may be attached to the catheter 10 via the handle 12 for operating the interventional device 38 or catheter 38' that operates the tool at the distal end of the catheter according to known structures and principles.

Figure 15:
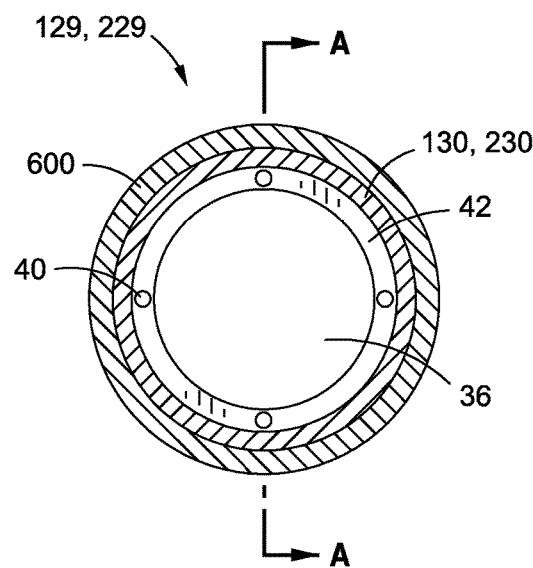
FIG. 15 is a typical sectional view of the segments shown in FIGS. 9-12.
Figure 16:
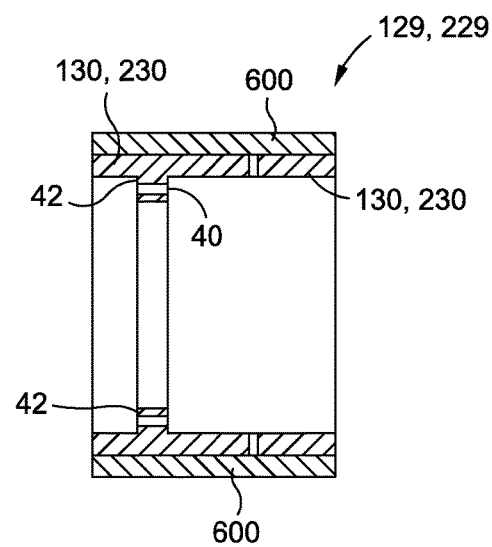
FIG. 16 is a sectional view of FIG. 15, taken substantially along the line A-A.

In other embodiments, as exemplified in FIGS. 9-10 and FIGS. 11-12, flexible segments 129, 229 respectively may be configured to provide some of the advantage that are provided by the embodiment of FIG. 5, and also other advantages. Here, flexible segments 129, 229 include cylindrical elements 130, 230 respectively, which are configured to move in relation to an adjacent cylindrical element by a revolute joint in a single plane. Each of these joints is also a bearing joint, in that, in these embodiments, each cylindrical element has two ball portions 132, 232 respectively and two mating socket portions 134, 234 respectively. (As used herein, ball portions are not necessarily balls in three dimensions, but at a minimum have a convex surface in two dimensions, and socket portions have a mating concave surface in two dimensions.) The ball portions are shaped to fit within the socket portions so that a convex surface of each ball portion bears upon an opposing concave surface of each socket portion so that the opposing surfaces slide past each other, or roll against each other, during rotation of the joint. Because each cylindrical element has two ball portions and two socket portions, rotation of the ball portions within the socket portions will impose a rotation of one cylindrical element with respect to another that is limited to a single plane. While a complete steerable assembly utilizing these embodiments of flexible segments 129, 229 is not shown in the figures, it will be appreciated that a complete steerable assembly can be constructed using the principles of the embodiment 28, while substituting the embodiment of the present segments 129, 229 for the previous segment embodiment 29. As will be seen, the embodiments 129, 229 do not include a pin or side snap passing through holes or depressions in two adjacent cylindrical elements for preventing axial movement of one cylindrical element in relation to another. However, in order to preserve axial stability, a flexible laminate or membrane 600 may be applied on the inside diameter, on the outside diameter, or on both the inside and the outside diameter of the segment 129, 229 (not shown in FIGS. 9-12, but FIGS. 15-16 exemplify a membrane 600 on the outside diameter). Application of the membrane may be by way of heat shrink wrap, or other suitable method. The laminate is configured to be sufficiently axially stiff to prevent axial separation of the cylindrical elements from each other, but permits rotation of the ball portion 132, 232 within the socket portion 134, 234 of each cylindrical element 130, 230 respectively. Under this configuration, the segments 129, 229 of these embodiments possess similar flexible qualities of the embodiment 29 in FIG. 5. Thus, a steerable assembly may be constructed to include one or more segments 129, 229 that are connected to each other by a special cylindrical element in which the axis joining the ball portions and the axis joining the socket portions are rotated by preferably 90 degrees. An exemplary special element suitable for this purpose may be seen to be found in elements 130a, 230a in FIGS. 13-14 respectively. It will be appreciated that the elements 130a and 230a possess a similar configuration to element 30a for rotating a bending angle of adjacent segments. The result is that one segment bends in a first single plane, and a second segment bends in a second single plane, and the first single plane and the second single plane may be rotationally offset at, preferably, 90 degrees to each other. This embodiment in which a ball and socket are used will facilitate ease of assembly of a segment because all that is required is to slip the cylindrical elements over a mandrel in the appropriate configuration so that all the balls reside in all the sockets, after which a membrane may be applied to the outer surface to hold the segment axially together. Of course, before the elements are slipped over a mandrel, pullwires may be inserted into the bore of each element as required, and fitted into detents provided.

Figure 13:
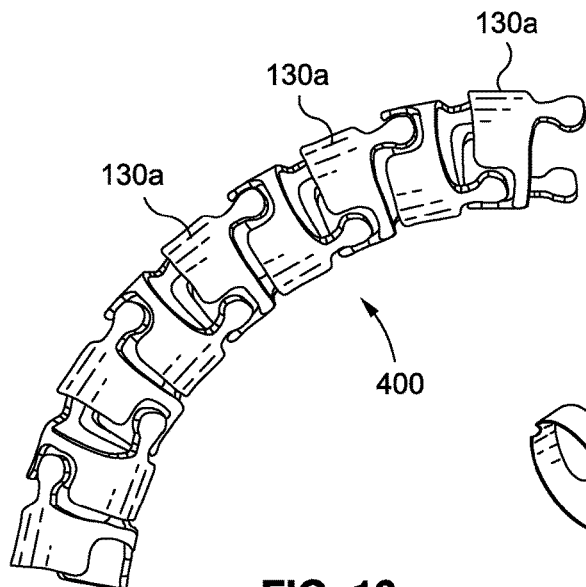
FIG. 13 is a perspective view of yet another embodiment of a segment of the invention, shown in a curved condition.
Figure 14:
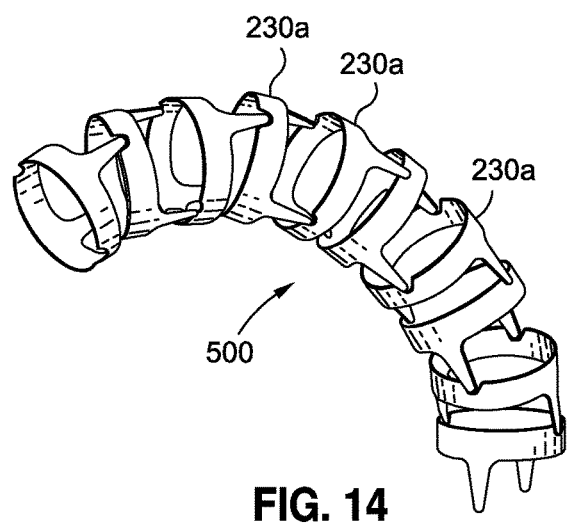
FIG. 14 is a perspective view of yet another embodiment of a segment of the invention, shown in a curved condition.

In yet further embodiments of the invention, exemplified in FIGS. 6, 13, and 14, a steerable element for a distal end of a catheter is described comprising cylindrical elements configured differently from the previous embodiments, yet having certain advantages of the previous embodiments, and also different advantages as described herein. In the embodiment exemplified in FIG. 6, a series of cylindrical elements 30a are connected together in series. Here, each cylindrical element is the same as the previous element, however as previously described with reference to special cylindrical element 30a that is seen in FIGS. 7 and 8, the elements are configured so that although a revolute joint in a single plane is provided in the joint between each element and the next, the single plane of each successive joint is rotated, preferably by 90 degrees. As will be appreciated, in this embodiment, each cylindrical element may have the form of the "special element" 30a which is described above. Thus, in FIG. 6, the entire steerable assembly is made up of special elements 30a, each one being configured to provide a revolute joint in single plane offset from the single plane of the previous joint by 90 degrees. In variations of the embodiment of FIG. 6, embodiment 400 is shown in FIG. 13 made up of special elements 130a, and embodiment 500 in FIG. 14 is made up of special elements 230a. In the latter two embodiments, ball portions and socket portions are provided as in previous embodiments, but here the two axes extending across the two balls and the two sockets of each cylindrical element 130a, 230a are rotated by 90 degrees in relation to each other to provide the described result. During manufacture and assembly of the embodiment of FIGS. 13 and 14, pullwire sets of the kind described above (although not shown in FIGS. 13 and 14) may be added as described above, via a flange 42 defining detents 40 configured to support opposing pullwire sets 44, 45 along a surface adjacent the inside diameter of the bore 36 extending through the assembly. Furthermore, a flexible membrane 600 may applied to restrain the cylindrical elements 130a and 230a against axial movement, but sufficiently flexible to permit rotational movement. In further embodiments, a membrane may be also applied to the embodiments of FIGS. 5 and 6 in the event that axial movement requires restraint.

It will be appreciated with respect to the embodiments of FIGS. 6, 13, and 14 that, because the single planes of each revolute joint alters direction by 90 degrees at every cylindrical element, a steerable assembly composed of these segment embodiments will not tend to adopt a single preformed shape such as is exemplified in FIG. 8. Rather, the tip of a steerable assembly composed of these embodiments will permit being directed by a physician in practically any lateral bending direction, upon appropriate application of the pullwire sets 44, 45. The present embodiment may therefore be conveniently used on its own at the distal end of a catheter, or it may be combined to form the distal tip, or other component, added to a steerable assembly formed according to the previous. Thus, a combination of features to a steerable assembly may be provided according to the principles of the disclosed embodiments to achieve the best advantage in a desired situation. In that regard, it will be understood that, although certain different features of the invention are described under different embodiments, the present invention may include a combination of such embodiments which are not necessarily described herein as being collected into a single embodiment.

In all cases of the cylindrical elements of the various embodiments may be formed from a polymer (e.g. Ultem®/PEEK). If additional strength is required, the polymeric elements can be insert molded with a metal, especially around the area of the detents for the pullwires. The elements may be molded, or machined, or a combination of both. In alternative embodiments, the elements maybe formed from a metal.

Thus, the steerable assembly provides an advantageous structure for navigating tortuous paths and thereafter adopting fixed shapes. The present invention may, of course, be carried out in other specific ways than those herein set forth without departing from the essential characteristics of the invention. The present embodiments are, therefore, to be considered in all respects as illustrative and not restrictive, while the scope of the invention is set forth in the claims that follow.

We claim:

1. A catheter configured for intraluminal delivery to a location in the body of a patient, the catheter comprising:
   an elongate hollow tubular body having a proximal end and a distal end;
   a steerable assembly attached to the distal end of the tubular body;
   wherein
   the steerable assembly comprises a first segment connected to a second segment;
   the first segment comprises a first element and a second element, each of the first element and the second element defining an internal bore and connected to each other by a first revolute joint in a single plane, characterized in that the single plane of the first revolute joint in a single plane is a first single plane, and further wherein the first revolute joint in a single plane is also a bearing joint;
   the second segment comprises a third element and a fourth element each of the third element and the fourth element defining an internal bore and connected to each other by a second revolute joint in a single plane, characterized in that the single plane of the second revolute joint in a single plane is a second single plane, and wherein the second revolute joint in a single plane is also a bearing joint;
   wherein the first single plane and the second single plane are offset by an angle from each other; and
   further wherein, each of the internal bores of the first element, the second element, the third element, and the fourth element are sized and configured to receive a clip device for performing mitral valve repair.

2. The catheter of claim 1, wherein the first segment further comprises:
   a fifth element defining an internal bore, and connected to the second element by a third revolute joint in a single plane, characterized in that the single plane of the third revolute joint in a single plane is the first single plane, and wherein the third revolute joint in a single plane is also a bearing joint;

a sixth element defining an internal bore, and connected to the fourth element by a fourth revolute joint in a single plane, characterized in that the single plane of the fourth revolute joint in a single plane is the second single plane, and wherein the fourth revolute joint is also a bearing joint.

3. The catheter of claim 1, wherein the offset angle is 90 degrees.

4. The catheter of claim 1, wherein the first segment and the second segment are connected to each other by an intermediate element.

5. The catheter of claim 1, wherein the first revolute joint in a single plane is formed to include a first opening in the first element and a second opening in the second element, and a pin passing through the first opening and the second opening.

6. The catheter of claim 1, wherein the first revolute joint is formed to include a depression in the first element and a protrusion on the second element, wherein the protrusion is configured to fit within the depression to permit rotation of the elements with respect to each other.

7. The catheter of claim 1, wherein the first revolute joint is formed to include a ball portion on the first element and a socket portion on the second element, wherein the socket portion is configured to receive the ball portion and to permit the ball portion to rotate while in contact with the socket portion.

8. The catheter of claim 1, wherein the steerable assembly further includes a flexible membrane configured to permit the elements of the steerable assembly to rotate in relation to each other, but to restrain the elements from axial movement in relation to each other.

9. The catheter of claim 8, wherein the flexible membrane is applied at an outside diameter surface of the steerable assembly.

10. The catheter of claim 1, further including a plurality of pullwires extending through the tubular body and through the steerable assembly, wherein each of the first element, second element, third element and fourth elements defines at least one detent configured to receive one of the plurality of pullwires.

11. The catheter of claim 10, wherein the at least one detent is a hole defining a complete continuous circumference.

12. A catheter configured for intraluminal delivery to a location in the body of a patient, the catheter comprising:
  an elongate hollow tubular body having a proximal end and a distal end;
  a steerable assembly attached to the distal end of the tubular body and comprising a first element, a second element, and a third element, each of the first element, the second element and the third element defining an internal bore, wherein
  the first element and the second element are connected to each other by a first revolute joint in a single plane characterized in that the single plane of the first revolute joint in a single plane is a first single plane, and wherein the first revolute joint in a single plane is also a bearing joint; and
  the second element and the third element are connected to each other by a second revolute joint in a single plane characterized in that the single plane of the second revolute joint in a single plane is a second single plane, and wherein the second revolute joint in a single plane is also a bearing joint and further wherein the first single plane and the second single plane are offset from each other by an angle; and, further wherein, each of the internal bores of the first element, the second element, and the third element are sized and configured to receive a clip device for performing mitral valve repair.

13. The catheter of claim 12, wherein the offset angle is 90 degrees.

14. The catheter of claim 12 wherein the first revolute joint in a single plane is formed to include a first opening on the first element and a second opening on the second element, and a pin passing through the first opening and the second opening.

15. The catheter of claim 12 wherein the first revolute joint is formed to include a depression in the first element and a protrusion on the second element, wherein the protrusion is configured to fit within the depression to permit rotation of the elements with respect to each other.

16. The catheter of claim 12, wherein the first revolute joint is formed to include a ball portion on the first element and a socket portion on the second element, wherein the socket portion is configured to receive the ball portion and to permit the ball portion to rotate while in contact with the socket portion.

17. The catheter of claim 12, further including a plurality of pullwires extending through the tubular body and through the steerable assembly, and wherein each of the first element, second element, and third element defines at least one detent configured to receive one of the plurality of pullwires.

18. The catheter of claim 12, wherein the steerable assembly further includes a flexible membrane configured to permit the elements of the steerable assembly to rotate in relation to each other, but to restrain the elements from axial movement in relation to each other.

19. The catheter of claim 18, wherein the flexible membrane is applied to an outside diameter surface of the steerable assembly.

20. A catheter configured for intraluminal delivery to a location in the body of a patient, the catheter comprising:
  an elongate hollow tubular body having a proximal end and a distal end;
  a steerable assembly attached to the distal end of the tubular body;
  a plurality of pullwires extending through the tubular body and through the steerable assembly; wherein
  the steerable assembly comprises a first segment connected to a second segment;
  the first segment comprises a first element and a second element connected to each other by a first revolute joint in a single plane characterized in that the single plane of the first revolute joint in a single plane is a first single plane and wherein the first revolute joint in a single plane is also a bearing joint;
  the second segment comprises a third element and a fourth element connected to each other by a second revolute joint in a single plane characterized in that the single plane of the second revolute joint in a single plane is a second single plane and wherein the second revolute joint in a single plane is also a bearing joint, wherein the first single plane and the second single plane are rotationally offset by an angle from each other; and
  wherein each of the first, second, third and fourth elements defines means for holding the plurality of pullwires at a predetermined location in relation to the elements; and
  further wherein, each of the first element, the second element, the third element, and the fourth element define an internal bore sized and configured to receive a clip device for performing mitral valve repair.

21. The catheter of claim 20, wherein each element is provided with a space that will allow one element to freely rotate to a limited degree in relation to an adjacent element.

22. The catheter of claim 20, wherein the offset angle is 90 degrees.

23. The catheter of claim 20, wherein the first element and the second element are connected in the first revolute joint in a single plane to each other by at least one pin passing through a first hole in the first element and a second hole in the second element, whereby the first element and the second element rotate about the at least one pin.

24. The catheter of claim 20, wherein the first element defines a ball portion and the second element defines a socket portion, wherein the socket portion is configured to receive the ball portion and to permit the ball portion to rotate while in contact with the socket portion.

25. The catheter of claim 20, wherein the first segment and the second segment are each connected to an intermediate element, wherein the intermediate element and the first segment are connected by a third revolute joint in the first single plane, and the intermediate element and the second segment are connected by a fourth revolute joint in the second single plane.

26. The catheter of claim 20, wherein the steerable assembly further includes a flexible membrane configured to permit the elements to rotate in relation to each other, but to substantially restrain the elements from axial movement in relation to each other.

27. The catheter of claim 26, wherein the flexible membrane is applied to an outside diameter surface of the steerable assembly.

28. The catheter of claim 20, wherein the means for holding the plurality of pullwires is four detents, and the plurality of pullwires is four pullwires in number, each detent being spaced apart from an adjacent detent.

* * * * *